(12) United States Patent
Wiedenmeier et al.

(10) Patent No.: US 6,196,069 B1
(45) Date of Patent: Mar. 6, 2001

(54) SPHERICAL SHOE PROOF TEST

(75) Inventors: Martin Wiedenmeier; William P. MacNutt; Peter Strzepa, all of Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/154,811

(22) Filed: Sep. 17, 1998

(51) Int. Cl.[7] ................................... G01N 3/02
(52) U.S. Cl. .................... 73/856; 73/81; 73/818
(58) Field of Search ................... 73/78, 81, 87, 73/12.01, 12.08, 12.09, 812, 830, 831, 834, 838, 845, 848, 849, 851, 855, 856

(56) References Cited

U.S. PATENT DOCUMENTS

| | | | |
|---|---|---|---|
| 1,596,003 | * 8/1926 | Davis | 73/81 |
| 2,986,926 | * 6/1961 | Freemon | 73/87 |
| 3,874,228 | * 4/1975 | Fatt | 73/816 |
| 4,201,078 | * 5/1980 | Morinaga | 73/12.09 |
| 4,692,165 | 9/1987 | Bokros | 623/2 |
| 4,863,458 | 9/1989 | Bokros | 623/2 |
| 5,336,259 | 8/1994 | Waits et al. | 623/2 |
| 5,351,552 | * 10/1994 | Giometti | 73/824 |
| 5,459,767 | * 10/1995 | Lessing | 376/245 |
| 5,507,189 | * 4/1996 | Kim et al. | 73/838 |
| 5,616,848 | * 4/1997 | Hemingway et al. | 73/838 |

* cited by examiner

Primary Examiner—Max Noori
(74) Attorney, Agent, or Firm—Timothy L. Scott; Philip S. Lyren; Kenneth S. Barrow

(57) ABSTRACT

An apparatus and method of proof testing a planar, brittle materials such as those used for valve leaflets in the manufacture of mechanical heart valve prostheses, in which the material to be tested is placed between two interfitting, spherically-shaped shoes, one convex and one concave, and the shoes are compressed together, causing a biaxial stress force to be applied across the surface of the material. The use of a biaxial force created by the spherical shoe surfaces simplifies the testing procedure over the prior art, allowing a single application of force to test the material for flexure in any direction. The magnitude of the stress which is applied to the material is determined by the radii of the interfitting test shoes relative to the thickness of the material sample being tested. Sufficient force is applied to conform the material to the shoes such that any flaws of a predetermined minimum critical size will be revealed by acoustical monitoring during the test or visual inspection thereafter.

10 Claims, 2 Drawing Sheets

SPHERICAL SHOE PROOF TEST

BACKGROUND

This invention relates generally to the manufacture of medical devices, and specifically to the testing of generally flat components of medical devices, e.g., the leaflets of mechanical heart valve prostheses. These valves have a generally rigid frame and at least one generally rigid leaflet operatively attached to the frame so that, in the closed position, the leaflet contacts adjacent leaflets and/or the valve frame thereby closing the valve and preventing the flow of blood therethrough. In one design, two semicircular hinged leaflets pivot within groves or other geometry contained in the orifice housing. In the open position, the leaflets separate from each other, and open radially outward toward the inner walls of a body lumen in which the valve is located. Examples of these designs are disclosed in U.S. Pat. Nos. 4,233,690; 4,689,046; 4,692,165; and 4,863,458; all of which are incorporated herein by reference.

One of the most common materials presently in use for forming these leaflets is Pyrolite® carbon. In one use, an inner graphite core is surrounded with Pyrolite® carbon, forming two outer layers. The formed Pyrolite® carbon pieces may have small flaws that are undetectable without a proof test. The proof test ensures that only the highest quality material is used in this medical device, preventing the chance for mechanical failure during the operational lifetime of the device.

A proof test is necessary to determine whether a planar, generally brittle material, e.g., a Pyrolite® carbon mechanical heart valve leaflet, contains flaws at or above a critical flaw size which might affect the operational life of the valve. The presence of flaws of such a critical size for Pyrolite® valve leaflets can be determined by exposing the leaflet to an appropriate stress field.

Prior art proof tests use a pair of mated cylindrical molds called "shoes" that apply a uniaxial stress field across the surface of a planar leaflet. These prior art tests using cylindrical-shaped shoes require four separate orientations on both flat surfaces to adequately proof test the leaflet. The leaflet to be tested is placed between the mated shoes, and a compressive load is placed on the leaflet by pressing the shoes together. The load is then relieved, allowing the shoes to be separated and the leaflet repositioned to measure leaflet stress/strain in another direction. This process is repeated until at least four separate orientations were tested. If the leaflet breaks or cracks, it is discarded. Based on the geometry of the shoes, this process concentrates stress distribution along a single axis, and requires load testing in multiple orientations—a time-consuming process. Also, placement location of the leaflet between the cylindrical shoes is critical, adding further to the complexity and time involved in the test.

The proof test of the present invention improves the stress distribution across the leaflet surface under test, reduces testing time by reducing the need for repositioning the leaflet and generally simplifies flat leaflet proof testing.

SUMMARY OF THE INVENTION

The present invention provides an apparatus for testing the strength of planar surfaces such as leaflets of mechanical heart valve protheses.

All flat leaflets to be utilized in the manufacture of artificial heart valves are proof tested by exposure to elevated tensile stresses across their surfaces. This is achieved by conforming the leaflet between a mated pair of spherical, convex and concave molds which are called "shoes", and applying a compressive force to the mated shoes. These spherical shoes apply biaxial tensile stresses across the leaflet surface. A spherical shoe proof test provides a significant reduction in processing time and handling per leaflet when compared to a prior art cylindrical shoe proof test. Furthermore, a spherical shoe proof test provides a more uniform stress distribution across the surface of a flat leaflet, and placement of the leaflet between the shoes is not critical, since a uniform biaxial stress is applied during the test.

A key feature of the invention is the use of spherically-shaped mating shoes which results in biaxial stress testing of the leaflets. In one aspect of the invention, the three key steps in the test include: (1) determining the spherical shoe radius necessary to reveal defects greater than the critical flaw size; (2) placing the leaflet to be proof tested between mated spherically-shaped shoes; and (3) applying the predetermined loading so that the leaflet conforms to the spherical shape defined between the shoes. The radius of the surface of the mated shoes directly relates to the critical flaw size of the test material, which critical flaw size is a function of material composition and thickness. In one aspect of the invention, the test material is a pyrolitic carbon leaflet for a mechanical heart valve prosthesis.

In the method of practicing the invention, the planar, generally brittle material is inserted between two mating concave/convex shoes, and a compressive load is applied to the mated shoes so that the leaflet conforms to the shape of the shoes. If the leaflet does not crack or break during this process, it passes the proof test. Cracks or breaks are determined by (1) acoustical monitoring during loading, and (2) visual inspection after loading.

DESCRIPTION

Figure 1:
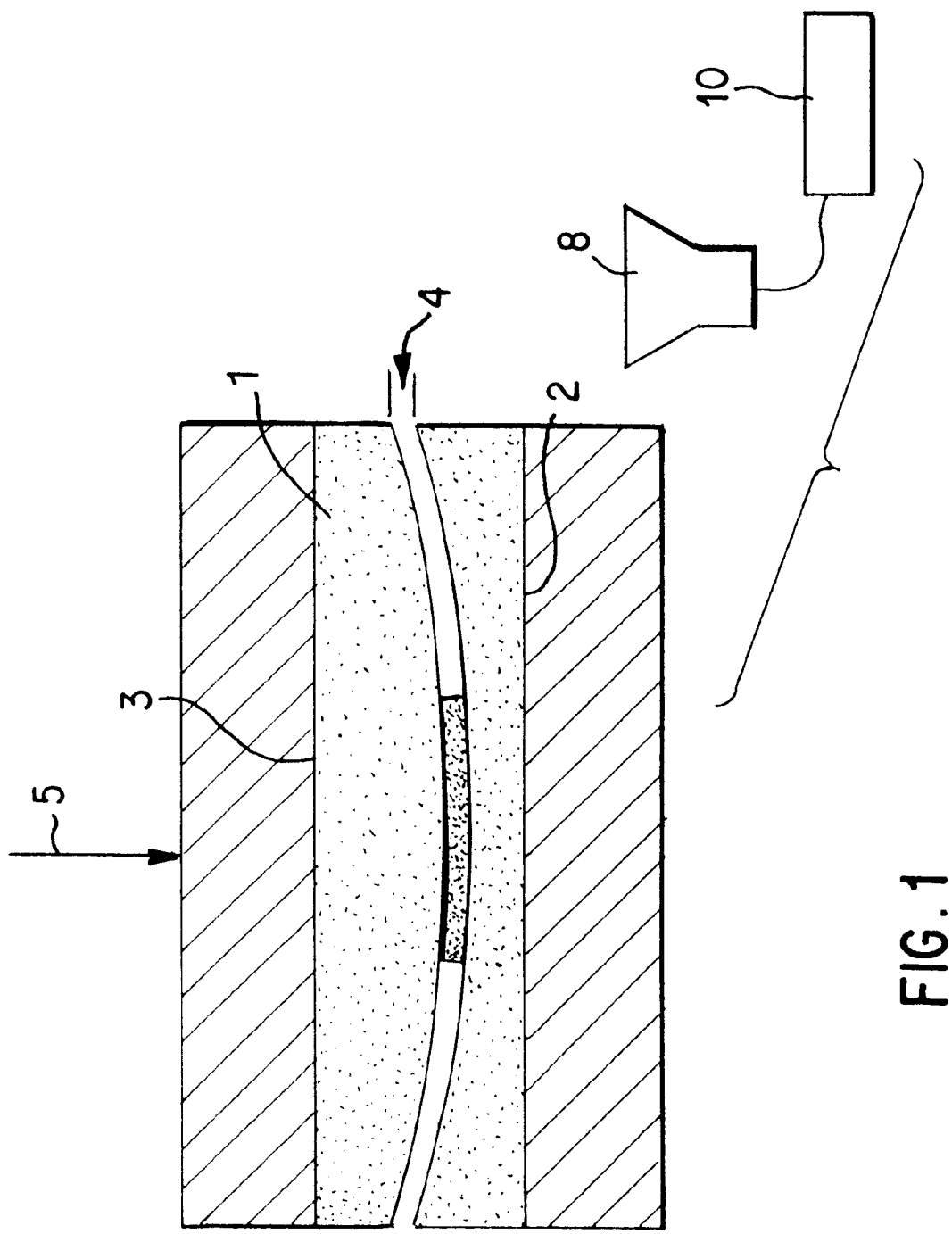
FIG. 1 is a sectional view showing the apparatus of the present invention, with a material to be tested between the upper and lower spherical shoe members.

The basic principle of operation of the spherical shoe proof test involves conforming the leaflet to be tested between a pair of spherical convex-concave shoes as shown in FIG. 1. Leaflet 3 is shown between upper spherical shoe 1 and lower spherical shoe 2. In order to eliminate contact damage to the leaflet during proof testing, these test shoes 1 and 2 are machined from non-scoring material, such as synthetic fluorine-containing resin, or linen phenolic resin composite.

To assure that leaflet 3 conforms to the spherical shoe shape, a load (indicated by arrow 5) is applied to upper shoe 1. Upon conformance of the leaflet to the space 4 defined between the upper and lower shoes, the maximum proof stress on the leaflet surface will be achieved. If the material does not crack or break during this process, the material passes the proof test. Cracks or breaks are detected by both visual inspection of the material after loading, and also acoustical monitoring during loading through the use of acoustic emissions sensor 8 mounted proximate shoes 1 and 2 and acoustic amplifier system 10. This proof stress is a direct function of the spherical shoe radii, which radii correlate to the load or displacement necessary to reveal defects greater than the critical flaw size of the test material. Determination of the appropriate shoe radii is described below.

Neglecting friction and shoe material compliance, the surface strain (s) imparted on the leaflet during spherical shoe proof testing can be expressed by the formula:

$$\epsilon = \frac{t}{2R}$$

where t is the leaflet thickness and R is the radius at the neutral axis of the leaflet.

Instead of a uniaxial stress imposed by prior art tests, the loaded spherical shoes 1 and 2 of the present invention creates a biaxial stress on the surface of the leaflets during proof testing. Since the shoes are semi-spherical, the strains ($\epsilon$) in the principal directions ("x" and "y" directions along the same plane) are equal, i.e., $\epsilon_x = \epsilon_y$. The relationship between stress and strains, therefore is given by the formula:

$$\sigma = \frac{E\epsilon}{1-v}$$

where $\sigma$ is the biaxial stress, $\epsilon = \epsilon_x = \epsilon_y$, and E and v are Young's modulus and Poisson's ratio, respectively. (E and v for Pyrolite® is $4.0 \times 10^6$ psi (27.6 Gpa), and 0.20, respectively.)

By combining equations 1 and 2, a relationship for calculating the shoe radius in terms of the induced stress can be written as:

$$R = \frac{tE}{2\sigma(1-v)}$$

Using an appropriate proof stress (determined from damage tolerance analysis, material properties, (i.e., crack growth rate, fracture toughness, Young's modulus, Poisson's ratio) and in-service stresses) and the minimum manufacturing thickness for valve leaflets, the radii of the spherical shoes can be calculated. These radii represent the radii necessary to reveal critical flaws therein.

Figure 2:
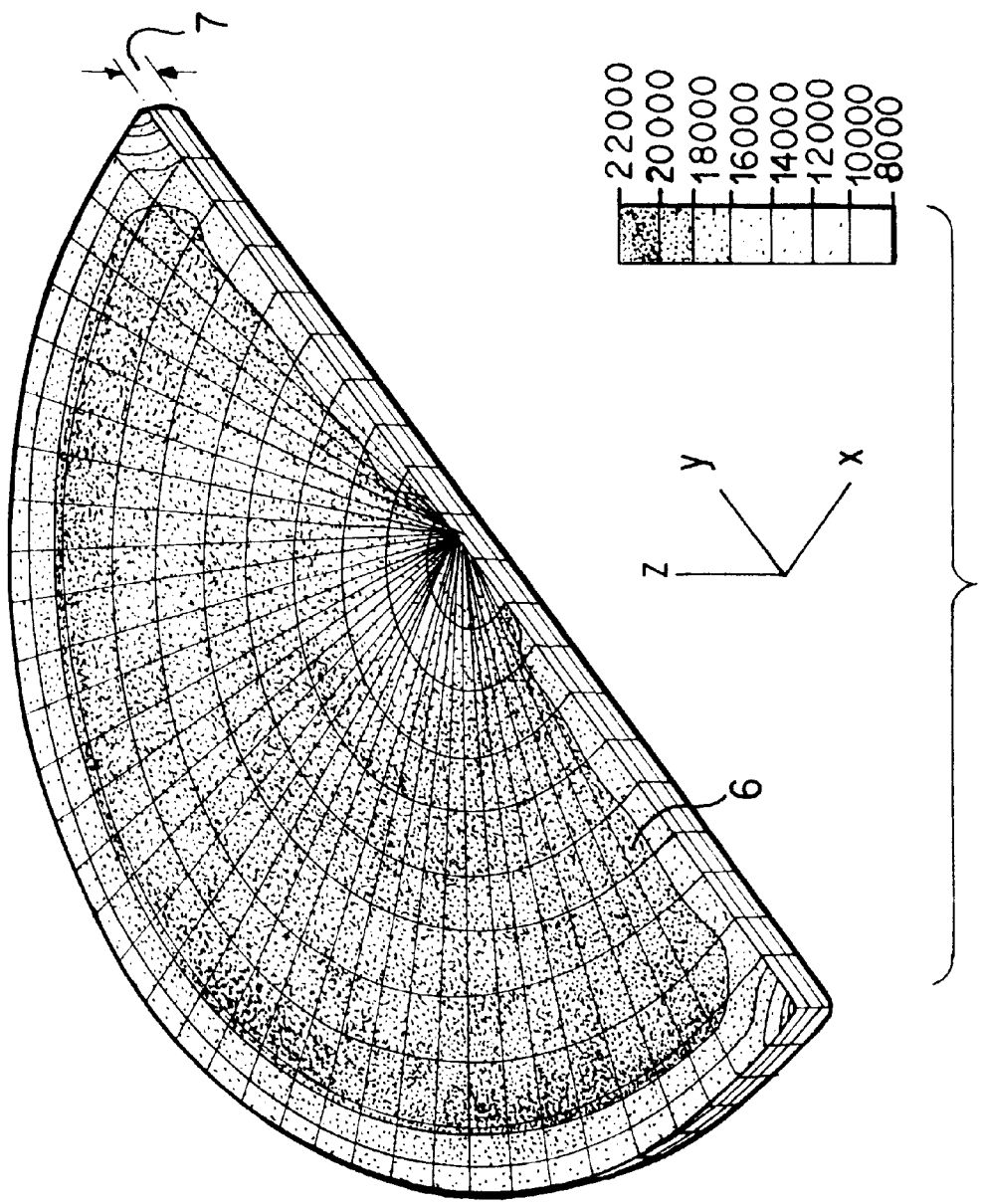
FIG. 2 is a Finite Element Analysis graph showing the resultant forces applied to a semicircular leaflet during a spherical proof test.

FIG. 2 shows the results of a typical finite element analysis (FEA) model of a Pyrolite® composite material with an applied biaxial load, where the stress units are measured in "psi". The geometry of the hypothetical test material is semicircular, with a thickness 7 and a radius corresponding to the dimensions of a leaflet for a "Size 29" mechanical heart valve prosthesis (the size corresponds to the tissue annulus diameter, in millimeters, at the implant location). As shown in shaded area 6, a proof stress of 20,000 psi (137.9 MPa) or higher is generally evenly distributed on at least 80% the leaflet surface area. Additional biaxial FEA models corresponding to Sizes 16 through 29 Pyrolite® composite mechanical heart valve prosthesis were created. The results for all leaflet sizes show the same large distribution of proof stresses, 20,000 psi or higher, across at least 80% of the leaflet surface.

The principal stresses from the FEA models were compared to actual measurements made using strain gages. Those tests show that the biaxial stresses applied to a valve leaflet under test by the spherical shoes of the invention can replace the uniaxial testing procedures of the prior art cylindrical shoe test as described above with greatly improved results, both simplifying the testing procedure and improving the accuracy thereof, and saving considerable time as well.

The scope of this invention should not be limited by the specifics utilized to describe the preferred embodiment as set forth above, but should be considered limited only be the breadth of the appended claims.

The invention claimed is:

1. A method of testing a planar, generally brittle material to determine the presence of flaws of a predetermined minimum size, the test comprising: (1) placing the planar material between a concave spherical shoe and a mating convex spherical shoe; and (2) applying a force to said shoes sufficient to conform said material to the spherical shoe shape, thereby applying a biaxial stress field to said material as said shoes are forced together.

2. The method of claim 1 further comprising the steps of determining the existence of cracks or breaks to said material.

3. The method of claim 2, in which the material to be tested comprises pyrolitic carbon.

4. The method of claim 2, in which the material to be tested constitutes a leaflet for use in an artificial heart valve.

5. The method of claim 2 where determining cracks or breaks is accomplished by acoustical monitoring.

6. The method of claim 1 wherein the force necessary to conform the planar material to the shoes is sufficient to reveal defects greater than a critical flaw size.

7. A method of proof testing a planar, generally brittle material to determine the presence of flaws by proof stressing said material into a spherical shape, wherein said stressing is accomplished by (1) placing said material between an upper spherical shoe and a lower spherical shoe, said upper shoe having a convex mating surface and said lower shoe having a matching concave mating surface, the radii of said upper and lower shoe members being determined by the thickness of the material being tested and the proof stress; and (2) compressing the upper and lower shoes to conform to said radii.

8. A proof test as set forth in claim 7, in which the results of said test are determined by acoustical monitoring during the test and by visual inspection of the tested material after completion of the test.

9. The method of claim 1 wherein said biaxial stress field is generally evenly distributed over at least 80% of said planar material.

10. The method of claim 1 wherein said planar material is smaller than said mating spherical shoes.

* * * * *